United States Patent [19]

Takamine

[11] Patent Number: 4,713,612
[45] Date of Patent: Dec. 15, 1987

[54] METHOD AND APPARATUS FOR DETERMINATION OF JUNCTION-TO-CASE THERMAL RESISTANCE FOR A HYBRID CIRCUIT ELEMENT

[75] Inventor: Henry Takamine, Gardena, Calif.

[73] Assignee: Hughes Aircraft Company, Los Angeles, Calif.

[21] Appl. No.: 885,502

[22] Filed: Jul. 14, 1986

[51] Int. Cl.$^4$ .................. G01N 25/00; G01R 31/26
[52] U.S. Cl. ................ 324/158 D; 364/557; 374/44
[58] Field of Search ............. 374/45, 29; 324/158 R, 324/158 D; 364/557

[56] References Cited

U.S. PATENT DOCUMENTS

| | | | |
|---|---|---|---|
| 3,745,460 | 7/1973 | Belzer et al. | 374/29 X |
| 3,842,346 | 10/1974 | Bobbitt | 324/73 R |
| 3,973,198 | 8/1976 | Hunt | 324/158 T X |
| 3,979,671 | 9/1976 | Meeker et al. | 324/158 F |
| 4,123,938 | 11/1978 | Hamilton | 374/29 |
| 4,604,572 | 8/1986 | Horiuchi et al. | 324/73 AF |

*Primary Examiner*—Daniel M. Yasich
*Attorney, Agent, or Firm*—Ronald L. Taylor; A. W. Karambelas

[57] ABSTRACT

A method and apparatus for determining the junction-to-case thermal resistance, $\theta_{jc}$, of a solid-state hybrid circuit element 38. First, the temperature coefficient, $T_c$, of the voltage across the junction is determined with a small calibration current flowing through the junction. Digital multimeters 12 and 28 are used to measure the junction voltage and current, respectively. Next, more power is applied and the total power, $P_T$, dissipated by the hybrid circuit element 38 is determined from values of the applied voltage and current measured with digital multimeters 12 and 14. The case of the hybrid element is kept at a constant temperature by a heat sink arrangement and the junction is allowed to reach thermal equilibrium at the higher power level. Finally, the increase in power to the hybrid element is removed and the change in junction voltage drop, $\Delta V_{BE}$, between low-power operation and high-power operation is determined using a storage oscilloscope 30. The junction-to-case thermal resistance, $\theta_{jc}$, is given by the quotient of $\Delta V_{BE}$ and the product of $P_T$ and $T_c$.

9 Claims, 6 Drawing Figures

METHOD AND APPARATUS FOR DETERMINATION OF JUNCTION-TO-CASE THERMAL RESISTANCE FOR A HYBRID CIRCUIT ELEMENT

GOVERNMENT RIGHTS IN INVENTION

The Government of the United States of America has rights in this invention pursuant to a government contract.

BACKGROUND OF THE INVENTION

1. Field of the Invention

The present invention relates to methods and apparatus for evaluating the power dissipation capabilities of solid-state circuit elements, and in particular to methods and apparatus for the determination of the junction-to-case thermal resistance, $\theta_{jc}$, of hybrid circuit elements.

2. Description of the Technology

An integrated circuit is normally encapsulated inside a plastic or metal package that has leads which can be soldered to a printed-circuit board or plugged into a connector. The working part of each package is only a small part of the volume, however. If each tiny integrated circuit is attached directly to a substrate rather than placed inside an individual package, several integrated circuits can be interconnected in circuits within a single package, thus eliminating the need for the printed-circuit board. Resistors can be fabricated on the substrate, and capacitors and discrete semiconductor elements can also be added, so that a completely self-contained interconnected circuit called a chip "hybrid" is formed.

A single hybrid can serve as a small, lightweight substitute for a printed-circuit board or collection of printed circuit boards, with the added benefit of considerably increased reliability. Hybrids have been widely used in aerospace and military applications. Other uses have been confined mostly to products produced in large volume, for example digital-to-analog converters and microwave communication circuits.

Hybrids are used for their increased reliability in applications such as cardiac pacemakers, telecommunications, automotive braking systems, and computer circuits. Hybrid reliability is generally regarded to be about ten times greater than that of an equivalent discrete circuit board.

The reliability of discrete components mounted on circuit boards suffers primarily from two failure mechanisms. First, the solder connections on the board can fail from from shock and vibration. Second, the semiconductor components are only lot-sample tested by manufacturers, so that some small number of faulty components are sent to any customer. Lot-samples are operated under load for only fractions of a second because more elaborate testing increases manufacturing costs prohibitively. Minimal tests are not good approximations of the conditions encountered by the components in service, however, and the user must therefore test each component to ensure reliability.

Hybrid interconnection methods reduce these problems. To eliminate solder connections, some monolithic hybrids have components formed within the substrate as in a large-scale integration chip. More often, components are chemically attached to the substrate. Chemical bonding methods are more reliable than making solder connections. Solder connections are still used on some hybrids, but far fewer are required than with discrete components on circuit boards. Most hybrids are encapsulated in epoxy, which further reduces the effects of mechanical vibration. The lot-sample testing problem with discrete integrated circuits is overcome by the fact that every hybrid comes in a complete package and can be readily tested.

The junction-to-case thermal resistance, $\theta_{jc}$, of a solid-state circuit element is of critical importance in circuit design and circuit component selection. A knowledge of its value is necessary for heat transfer calculations in the design of heat sinks to dissipate the power developed in a solid-state circuit element. Inadequate heat sinks designed on the basis of wrong values of $\theta_{jc}$ can result in disastrous consequences if crucial circuit elements fail in vital control and other types of circuits.

Previous methods of determining $\theta_{jc}$, have used direct current approaches that require repetitive testing followed by averaging of data. Such methods are time-consuming, inconvenient, and inefficient. There has been a long felt but unfulfilled need for a convenient yet quick and accurate method to determine the junction-to-case thermal resistance of hybrid solid-state circuit elements. Such a method would be a boon to the electronics industry and the large number of associated industries that require reliable electronic components for their products and for their manufacturing and test equipment.

SUMMARY OF THE INVENTION

The present invention solves the problem of providing a quick, accurate determination of the junction-to-case thermal resistance, $\theta_{jc}$, of hybrid solid-state circuit elements in a manner which is eminently suitable for automation.

First, a semiconductor p-n junction in the hybrid circuit element is found, and then the temperature coefficient, $T_c$, of the voltage across the junction versus temperature is determined with a small calibration current flowing through the junction. Next, more power is applied and the total power, $P_T$, dissipated by the hybrid circuit element is determined from measured values of the voltage and current applied to it. The case of the hybrid element is kept at a constant temperature by a heat sink arrangement and the junction is allowed to reach thermal equilibrium at the higher power level. Finally, the increase in power to the hybrid element is removed and the change in junction voltage drop, $\Delta V_{BE}$, between low-power operation (only calibration current flowing) and high-power operation (up to 40 V across the hybrid circuit element) is determined using a-storage oscilloscope. The junction-to-case thermal resistance, $\theta_{jc}$, is given by the quotient of $V_{BE}$ divided by the product of $P_T$ and $T_c$.

Therefore, it is an object of the present invention to provide apparatus for the rapid determination of the junction-to-case thermal resistance, $\theta_{jc}$, of a solid-state hybrid circuit element in a nondestructive way.

It is a further object of the present invention to provide a method of determining, in a simple and convenient way, the junction-to-case thermal resistance, $\theta_{jc}$, of a solid-state hybrid circuit element.

It is yet another object of the present invention to provide an adequate and cost-efficient means of thermal testing of solid-state hybrid circuit elements so that their reliability can be increased.

Another object of the present invention is to enable users of solid-state electronic components to determine whether their heat dissipation performance is within the specifications quoted by the manufacturer.

Finally, it is an object of the present invention to provide a method of determining the junction-to-case thermal resistance, $\theta_{jc}$, of a solid-state hybrid circuit element in a manner which readily lends itself to automation.

An appreciation of other aims and objects of the present invention and a more complete and comprehensive understanding of this invention may be achieved by studying the following description of a preferred embodiment and by referring to the accompanying drawings.

DESCRIPTION OF A PREFERRED EMBODIMENT

Figure 1:
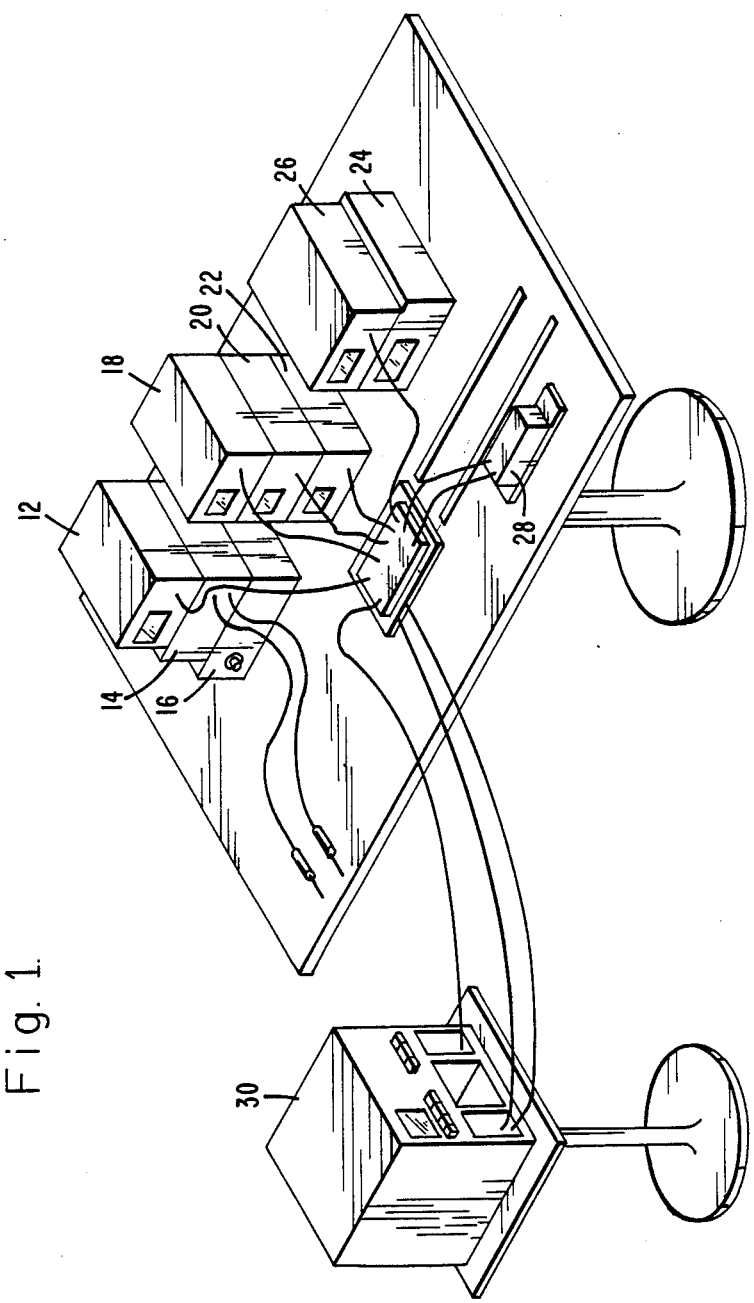
FIG. 1 is a drawing of the apparatus used in the present invention.

Referring to FIG. 1, the following pieces of equipment are used in the setup for measuring the junction-to-case thermal resistance of a hybrid semiconductor circuit element:

A first battery-operated Fluke model 8050A digital multimeter 12 to measure the dc voltage supplied to the hybrid circuit element, a second battery-operated Fluke model 8050A digital multimeter 14 to measure the dc current supplied to the hybrid circuit element, a Hewlett-Packard model 3310B signal generator 16 to generate a 2.5 MHz sine wave, a first Hewlett-Packard model 6216A dc power supply 18 to provide +5 Volts for a latch circuit, a second Hewlett-Packard model 6216A dc power supply 20 to provide −20 Volts, a third Hewlett-Packard model 6216A dc power supply 22 to provide +20 Volts, a Newport model 267A thermocouple-based digital temperature indicator 24, a third battery-operated Fluke model 8050A digital multimeter 26 to monitor the current through the p-n junction, a 5-Vblt battery 28 to supply calibration current, and a Tektronix model 7834 storage oscilloscope 30. The Tektronix model 7834 storage oscilloscope 30 has two plug-in units: a 7A22 differential amplifier with dc offset and a 7892A time base. Optionally, two other pieces of equipment may be of use: a Tektronix model 576 curve tracer (not shown in FIG. 1) for finding a semiconductor p-n junction or diode if the circuit diagram for the hybrid circuit element under test is not available, and a Tektronix model 7904 oscilloscope for checking to see that the normal operation of the hybrid circuit element is not disturbed in making measurements with the present invention.

Figure 2:
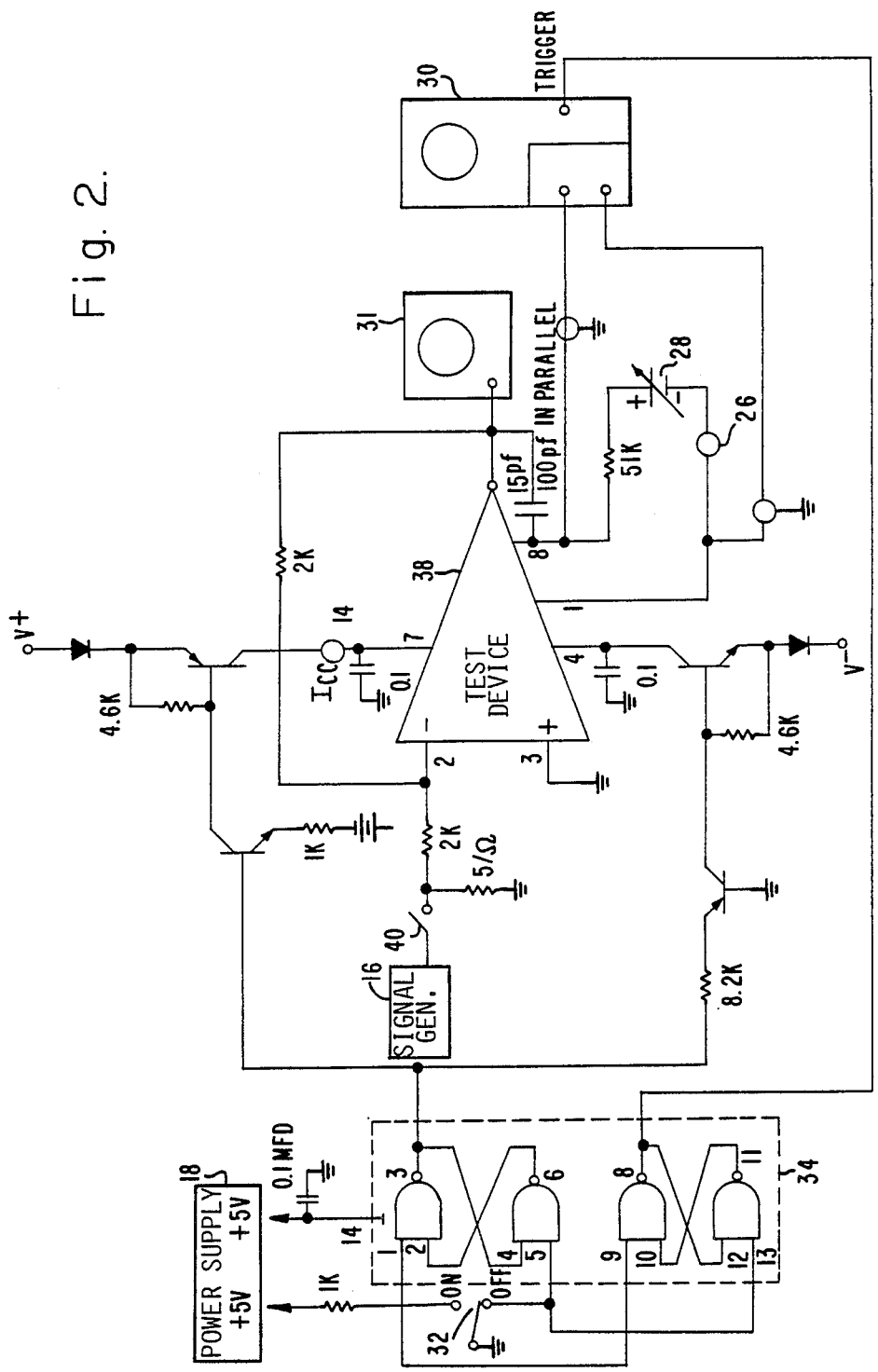
FIG. 2 is a schematic diagram of the electronic circuitry used in the present invention.

Referring to FIG. 2, a first on-off switching means 32 activates a 54H00 digital latch integrated circuit 34 at left in the figure. In an automated embodiment the switching means could be replaced by a digital integratedcircuit flip-flop. In the "on" position the switching means 32 allows power from the 20-volt dc supplies 20,22 to be applied to the solid-state hybrid circuit element 38, (labelled "Test Device" in FIGS. 2 and 3). In this example, the test divice 38 is a 9N05 Teledyne 1437. A Hewlett-Packard model 3310B 2.5 MHz sine-wave signal generator 16 is connected through a second switching means 40 to the input of the hybrid circuit element to check whether the hybrid circuit element operates correctly under normal biasing without being affected by the process of making measurements on the p-n junction. The details of this checking procedure will vary depending on the particular hybrid circuit element under test. The output voltage waveform from the hybrid is monitored with a Tektronix model 7904 oscilloscope 31. The calibration current of 0.1 mA supplied by the variable voltage source 28 (5 Vblts nominal) is set using the third digital multimeter 26 to monitor the current as shown in FIG. 2.

Figure 3:
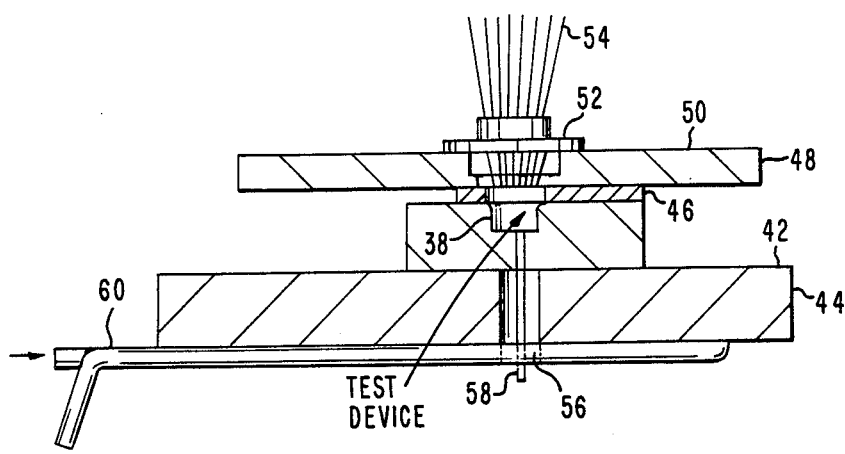
FIG. 3 is a sectional view of the arrangement of mounting the hybrid circuit element on the heat sink assembly which also shows the details of the thermocouple mounting and the tubing for water-cooling the copper heat sink.

Referring now to FIG. 3, the details of the mounting of the hybrid circuit element 38 on the heat sink assembly are shown. The case of the hybrid circuit element 38 fits into a countersunk recess in an aluminum heat sink plate 42 which in turn is attached to a larger copper heat sink plate 44. The bottom of the hybrid circuit element case fits into a hole in a Hughes Space and Communications Group number 3841025 heat sink plate 46 which is placed between the aluminum heat sink plate 42 and a copper-clad circuit board 48 on the copper-clad side 50 of which is attached a connector socket 52 for bringing out the electrical leads 54 from the case of the hybrid circuit element 38. Through a relief hole 56 in the copper heat sink plate 44 a thermocouple 58 is inserted so that it is in contact with the top of the case of the the hybrid circuit element 38. Thermal contact between the junction of the thermocouple 58 and the hybrid case top is effected by means of a silicone grease, any excess of which comes out of the relief hole 56. Copper tubing 60 with tapwater flowing through it is used to maintain a constant temperature for the case of the hybrid during the heavy-power-dissipation phase of the procedure.

Figure 4:
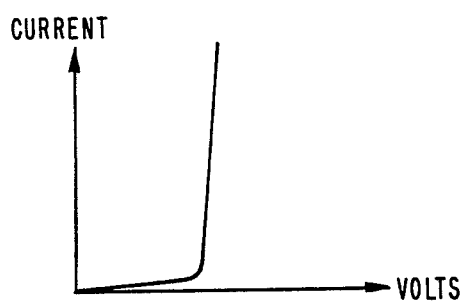
FIG. 4 is a typical graph of the current through a p-n semiconductor junction versus the potential difference across it.

The procedure of the present invention for determining the junction-to-case thermal resistance $\theta_{jc}$ of a solid-state hybrid circuit element is as follows:

First a semiconductor p-n junction or a diode is located somewhere in the hybrid circuit element, either by looking at a circuit diagram or by using a transistor curve tracer if the circuit diagram is not available. If the curve tracer is used, the input current is set at 10 microamperes, a value which avoids the noisy region of operation of the circuit but will not disturb any part of the circuit or destroy any sensitive component of it. With two electrical probes the hybrid circuit element is probed, two terminals or leads 54 at a time, until the output on the transistor curve tracer indicates that the diode-like behavior of a p-n junction has been found, as illustrated in FIG. 4. The junction that has been found is then used to generate the voltage versus temperature curve illustrated in FIG. 5 and described below.

The normal operation of the particular solid-state hybrid circuit element 38 chosen as an example is verified by checking its behavior as an amplifier for the case of a perfect 2.5-MHz sine-wave input from the frequency generator 16. Switching means 40 is in its "on" position for this test so that the sine wave is applied to the terminal labeled 2 of the hybrid element or test device 38 in FIG. 2. The maximum voltage per specification requirements is set by adjusting the outputs of the dc voltage supplies 20,22 and observing the total voltage between the terminals marke V+ and V− in FIG. 2 with the digital multimeter 12. The calibration current is set at 0.1 mA by adjusting the variable voltage supply 28 and observing the value indicated on the digital multimeter 26. The output of the solid-state hybrid circuit element 38 is monitored on the oscilloscope 31; a perfect sine-wave output indicates normal operation. For this part of the procedure the switching means 32 is in the "on" position as shown in FIG. 2.

Figure 5:
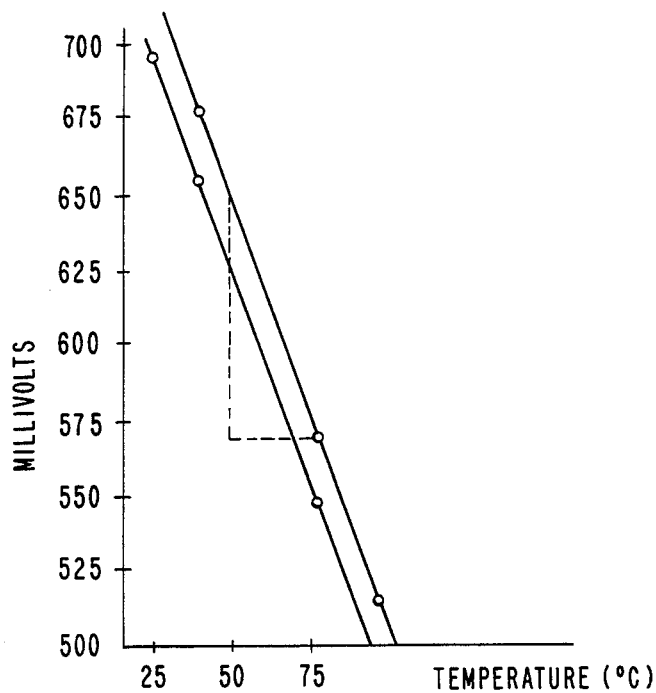
FIG. 5 shows plots of the potential drop in millivolts across p-n semiconductor junctions versus temperature in degrees Centigrade for two typical hybrid solid-state circuit elements. Note that the two solid lines drawn through the experimentally determined points (small open circles) are parallel. Their common slope represents the temperature coefficient $T_c$, which can be determined by measuring the ratio of the lengths of the dotted vertical and horizontal line segments.

Next the calibration curve is plotted so that the temperature coefficient $T_c$ can be determined from the slope of the straight line of the calibration curve. The switching means 32 is in the "off" position for this part of the procedure. A calibration curve of 0.1 mA is chosen as monitored on digital multimeter 26. Assuming an average of the voltage across the junction of 0.7 V, the power dissipated due to the calibration current would be 0.07 mW, a negligible amount. Using a suitable temperature chamber, such as a Delta Design model 3900 with a Type 5 controller, the hybrid is subjected to temperatures in the range from 40° to 100° C. At least four different values of temperatures are chosen, and at each chosen temperature the voltage drop across the p-n junction is measured with the same 0.1 mA calibration current flowing. A plot of junction voltage drop versus temperature is made, as illustrated by FIG. 5. The plot should be a straight line with negative slope, and the value of the slope is the temperature coefficient $T_c$. A knowledge of the temperature coefficient provides a "thermometer" for the chip.

The determination of junction-to-case thermal resistance $\theta_{jc}$ proceeds as follows:

The setup shown in FIG. 3 insures that the hybrid circuit element case temperature is constant before and during maximum power dissipation. The aluminum heat sink 42 attached to the water-cooled copper plate 44 is extremely efficient in removing heat generated during the heavy power dissipation period.

The hybrid circuit element 38 is connected to the test circuit as shown in FIG. 2 with switching means 32 in its "off" position and a current of 0.1 mA flowing through the digital multimeter 26. The cathode ray tube screen of the storage oscilloscope 30 should display a horizontal line which represents the no-power voltage of the base-to-emitter junction of the hybrid circuit element 38.

Figure 6:
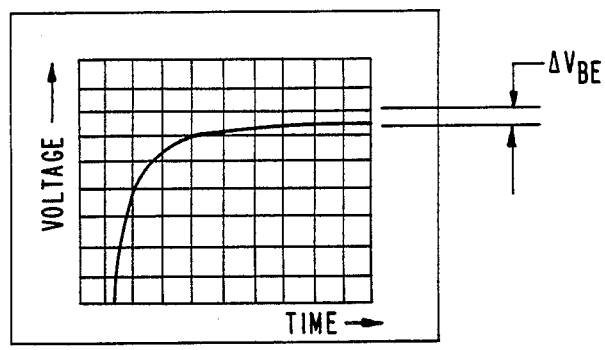
FIG. 6 is a drawing of a typical storage oscilloscope trace of base-to-emitter voltage $V_{BE}$ versus time. The vertical amplitude scale is 20 mV per division and the horizontal sweep scale is 1 ms per division.

Next the switching means 32 is set to its "on" position so that the integrated digital latch circuit 34 enables full power to be supplied to the hybrid circuit element. The second latch (the lower one in FIG. 2 at left) of the 54H00 integrated digital latch circuit 34 at this time resets the trigger of the storage oscilloscope 30. After the hybrid circuit element 38 reaches thermal equilibrium, switching means 32 is changed to its "off" position, so that power is removed from the hybrid circuit element 38 except for the 0.1 mA calibration current. At the instant the first latch turns power off, the second latch triggers the storage oscilloscope 30 so that a second base-to-emitter voltage trace is displayed, as shown in FIG. 6. The difference between the base-to-emitter voltage before and immediately after heavy power operation, $\Delta V_{BE}$, can now be determined from the traces on the screen of the storage oscilloscope 30. As can be seen from FIG. 6, the second trace shows a very steep slope indicating a heavy charge stored in the emitter-base junction. The steep slope gradually flattens out to a normal $V_{BE}$ display. The value of $\Delta V_{BE}$ at a point 3 ms after power-off is taken. The junction-to-case thermal resistance $\theta_{jc}$ of the hybrid circuit element 38 is determined by dividing $\Delta V_{BE}$ by the product of the thermal coefficient $T_c$ and the total power dissipation $P_T$:

$$\theta_{jc} = \Delta V_{BE}(T_c P_T) \tag{1}$$

Various aspects of the procedure described above can readily be automated, as can be appreciated by anyone ordinarily skilled in the art. Furthermore, the present invention has been described in detail with reference to a particular preferred embodiment, but persons possessing ordinary skill in the art to which this invention pertains will appreciate that various modifications may be made without departing from the spirit and scope of the invention.

What is claimed is:

1. A method for determining the junction-to-case thermal resistance $\theta_{jc}$ of a solid-state circuit element mounted in a case, the circuit element having at least one semiconductor p-n junction, including the steps of:
   (a) applying a calibration current through the junction;
   (b) measuring a voltage drop across said junction for a plurality of temperatures to determine a temperature coefficient $T_c$ with said calibration current flowing through said junction;
   (c) applying a substantial increase in power to said solid-state circuit element and allowing said solid-state circuit element to reach a state of thermal equilibrium with a surrounding environment;
   (d) measuring a total power dissipation $P_T$ of said solid-state circuit element while keeping said base of said solid-state circuit element at a constant temperature;
   (e) removing said increase in power to said solid-state circuit element and measuring a change in junction voltage drop $\Delta V_{BE}$ between low-power operation (only a small calibration current flowing) and high-power operation (substantially increased power to said solid-state circuit element); and
   (f) determining said junction-to-case thermal resistance $\theta_{jc}$ by dividing said $\Delta V_{BE}$ with the product of said total power $P_T$ and said temperature coefficient $T_c$.

2. The method recited in claim 1 in which said case is mounted in a water cooled fixture.

3. The method recited in claim 1 in which step (e) includes triggering a storage oscilloscope upon the removal of the increase in power.

4. A method for determining the junction-to-case thermal resistance of a solid state hybrid circuit element, said hybdrid circuit element being mounted in a case and including at least one semiconductor p-n junction, said method comprising the steps of:

(a) applying a calibration current through the junction;
(b) calculating a temperature coefficient for the junction;
(c) applying additional power to the circuit element and measuring the power dissipated thereby;
(d) lowering the power to the circuit element until only the calibration current is applied to the junction;
(e) measuring the voltage drop across the junction between steps (c) and (d); and
(f) determining the junction-to-case thermal resistance by dividing the voltage drop with product of the measured power dissipated by the circuit and the temperature coefficient of the junction.

5. The method of claim 4 wherein said case is maintained at substantially a constant temperature during at least step (c).

6. The method of claim 5 wherein said case is mounted in a water cooled fixture to maintain its temperature substantially constant.

7. The method of claim 4 wherein step (b) includes: measuring a voltage drop across the junction over a range of temperatures.

8. The method of claim 7 wherein step (e) includes: triggering a storage oscilloscope upon removal of the increase in power.

9. A method for determining the junction-to-case thermal resistance of a hybrid circuit element mounted in a case, the circuit element including at least one semiconductor p-n junction therein, said method including the steps of:
  (a) placing the circuit element in a fixture;
  (b) measuring changes in voltage across said junction as a function of temperature to thereby determine the temperature coefficient of said junction while a small calibration current is flowing therethrough;
  (c) measuring the voltage drop across the junction with said calibration curent flowing therethrough;
  (d) increasing the power to the circuit element;
  (e) measuring total power dissipation in said circuit element while maintaining the case at a substantially constant temperature;
  (f) thereafter, removing power to the circuit element except for said calibration current being applied to said junction;
  (g) measuring the voltage drop across the junction within about 3 seconds after the power is removed in step (f);
  (h) calculating the difference between the voltage drop across the junction measured in step (c) and step (g); and
  (i) determining the junction-to-case thermal resistance by dividing said voltage drop difference calculated in step (h) with the product of the total power dissipated as measured in step (e) and said temperature coefficient as measured in step (b).

* * * * *

UNITED STATES PATENT AND TRADEMARK OFFICE
CERTIFICATE OF CORRECTION

PATENT NO. : 4,713,612

DATED : December 15, 1987

INVENTOR(S) : Gina R. Kunkel, et al

It is certified that error appears in the above-identified patent and that said Letters Patent is hereby corrected as shown below:

On the first page of the patent, the inventors should be listed as follows:

Gina R. Kunkel, Redondo Beach; Michelle E. Talbert, Mountain View; Henry K. Takamine, Gardena, all of Calif.

Title page item [19] "Takamine" should read --Kunkel et al--.

Signed and Sealed this

Eighteenth Day of October, 1988

*Attest:*

DONALD J. QUIGG

*Attesting Officer*      *Commissioner of Patents and Trademarks*